United States Patent [19]

Ryaby et al.

[11] 4,266,532
[45] May 12, 1981

[54] MODIFICATION OF THE GROWTH, REPAIR AND MAINTENANCE BEHAVIOR OF LIVING TISSUES AND CELLS BY A SPECIFIC AND SELECTIVE CHANGE IN ELECTRICAL ENVIRONMENT

[75] Inventors: John P. Ryaby, Essex Falls; Arthur A. Pilla, Wyckoff, both of N.J.

[73] Assignee: Electro-Biology, Inc., Fairfield, N.J.

[21] Appl. No.: 887,485

[22] Filed: Mar. 17, 1978

Related U.S. Application Data

[63] Continuation-in-part of Ser. No. 742,706, Nov. 17, 1976, Pat. No. 4,105,017, which is a continuation-in-part of Ser. No. 633,408, Nov. 19, 1975, abandoned.

[51] Int. Cl.³ ............................................. A61N 1/40
[52] U.S. Cl. ..................................... 128/1.5; 128/82.1; 128/419 F; 128/421; 128/802
[58] Field of Search .................... 128/1.3, 1.5, 82.1, 128/419 F, 419 R, 420 R, 421–423, 783, 802, 804; 219/10.79

[56] References Cited

U.S. PATENT DOCUMENTS

| | | | |
|---|---|---|---|
| 1,637,829 | 8/1927 | Lurie | 128/802 |
| 2,404,283 | 7/1946 | Gieringer | 128/804 |
| 2,583,853 | 1/1952 | Kazdin | 128/804 |
| 2,882,904 | 4/1959 | Rasmussen | 128/804 X |
| 3,890,953 | 6/1975 | Kraus et al. | 128/1.5 |
| 3,893,462 | 7/1975 | Manning | 128/1.5 |
| 3,915,151 | 10/1975 | Kraus | 128/1.5 |
| 4,056,097 | 11/1977 | Maass | 128/1.5 |

OTHER PUBLICATIONS

Bassett et al., "A Non-Operative . . . Electromagnetic Fields", Clin. Orth., May 1977, vol. 124, pp. 128-143.
Bassett et al., "Augmentation of Bone Repair . . . ", Science, vol. 184, pp. 575-577, May 3, 1974.

Primary Examiner—Lee S. Cohen
Attorney, Agent, or Firm—Hopgood, Calimafde, Kalil, Blaustein & Lieberman

[57] ABSTRACT

Surgically non-invasive method of and apparatus for altering the growth, repair and maintenance behavior of living tissues and/or cells by inducing voltage and concomitant current pulses of specific time-frequency-amplitude relations therewithin.

31 Claims, 23 Drawing Figures

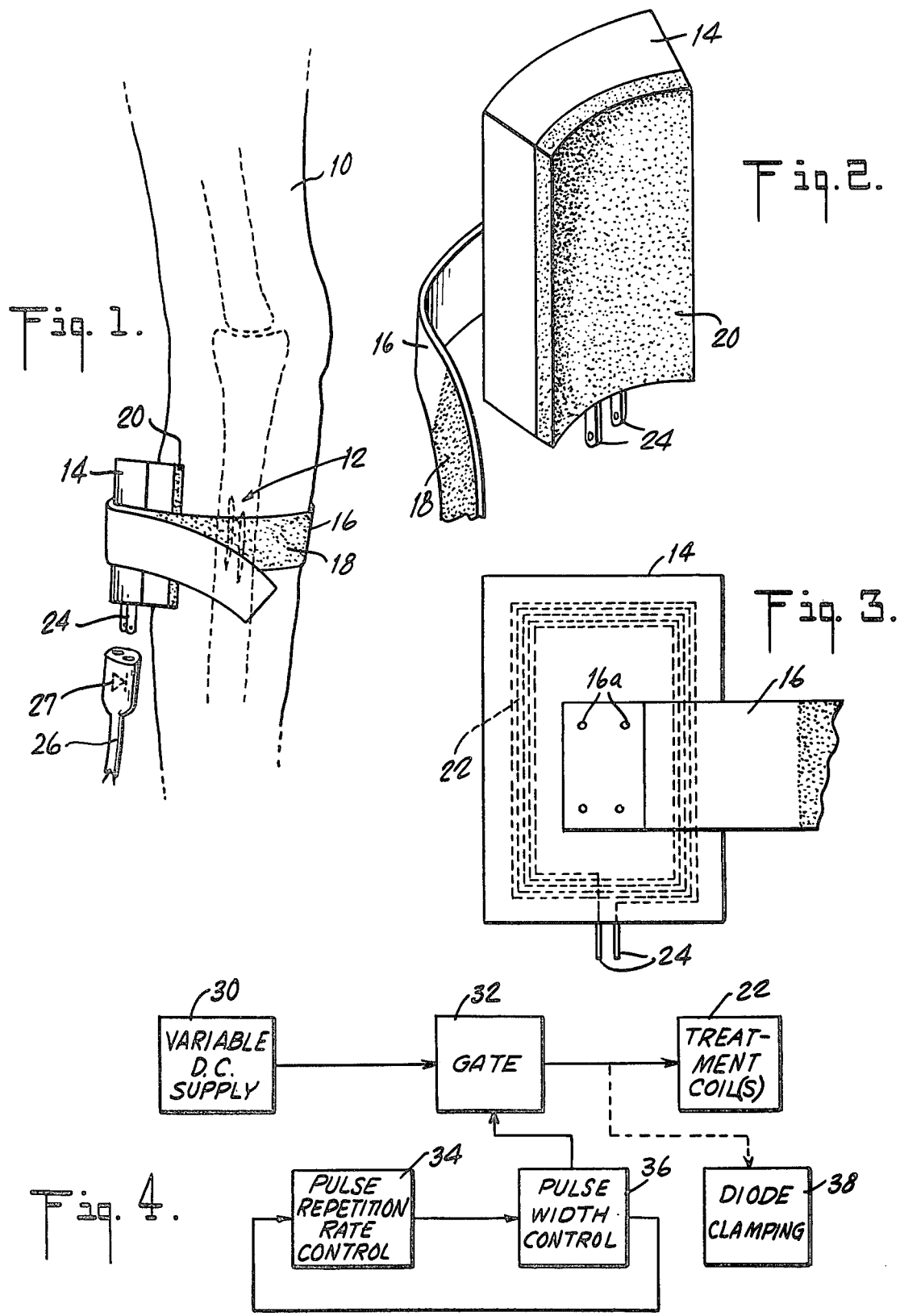

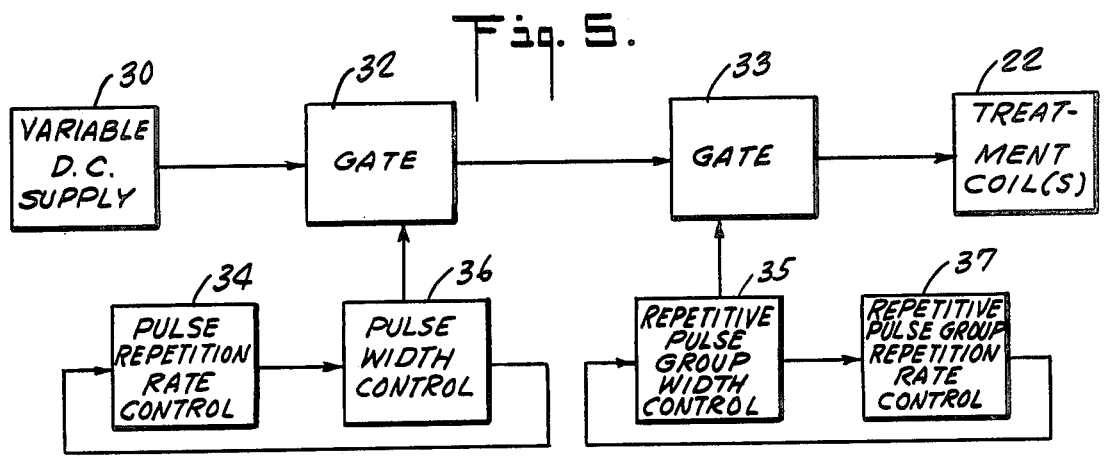
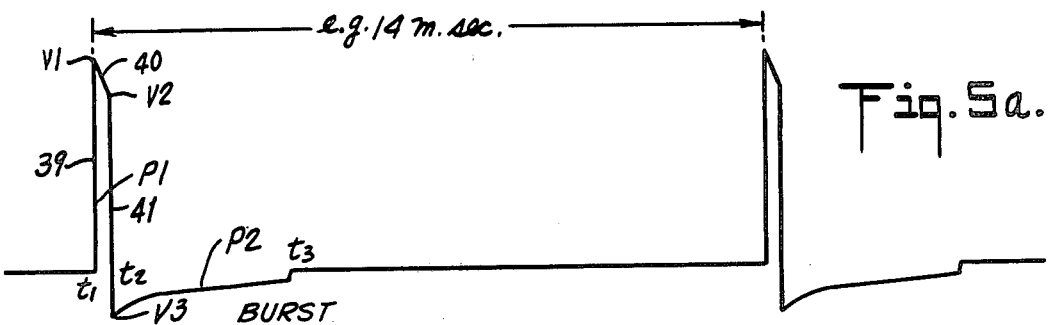
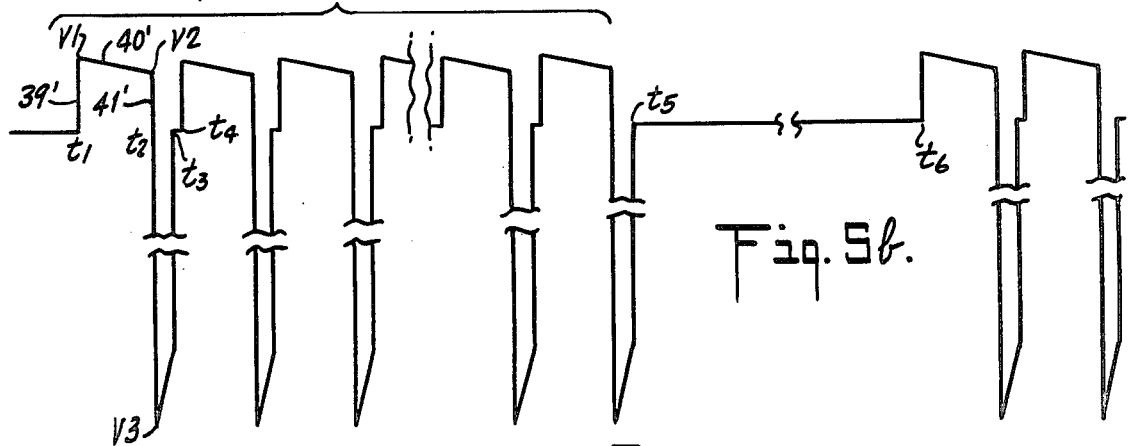
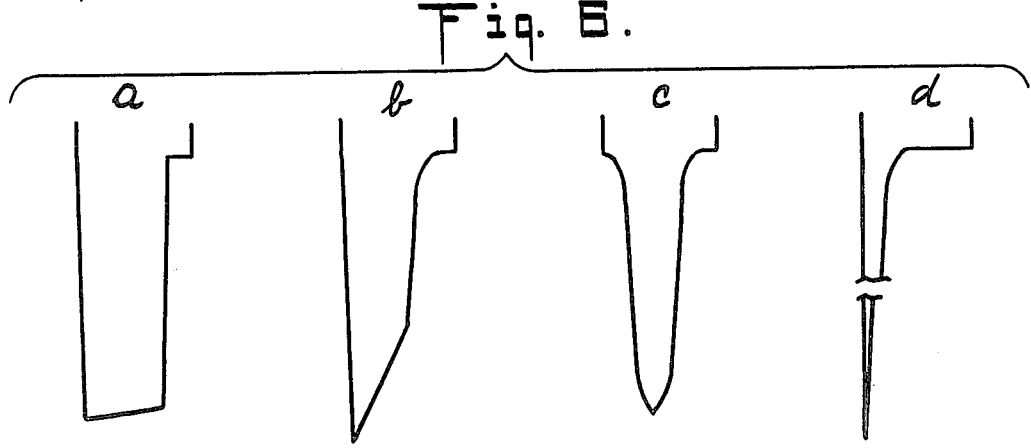

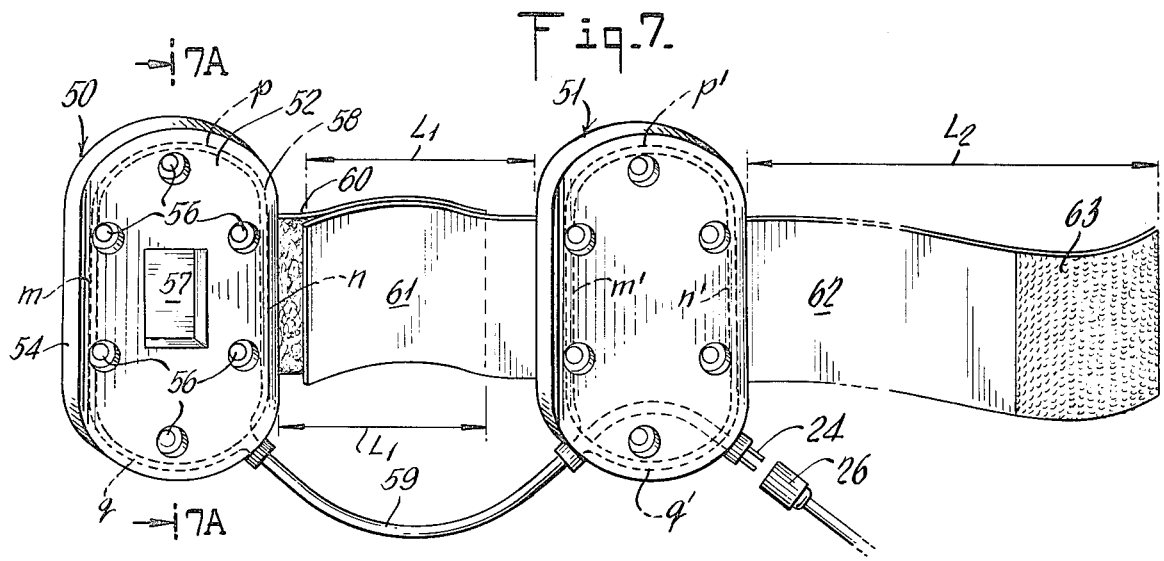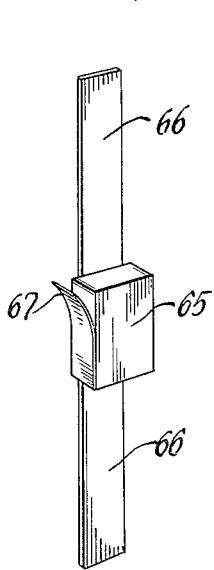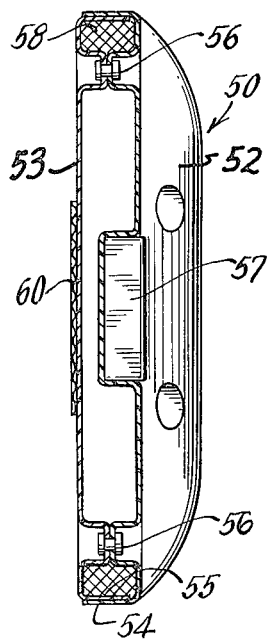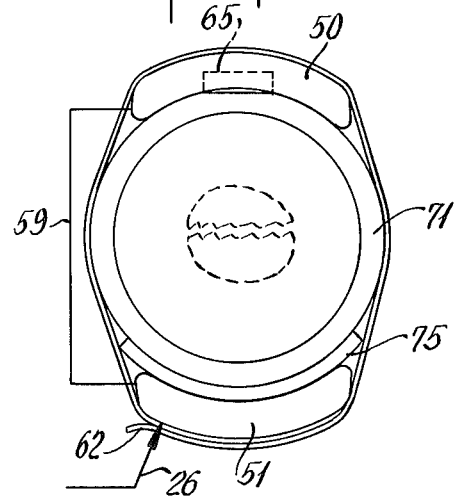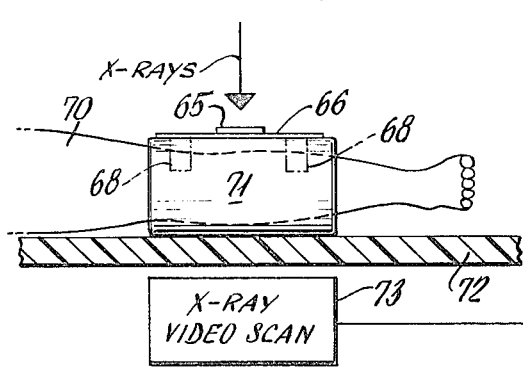

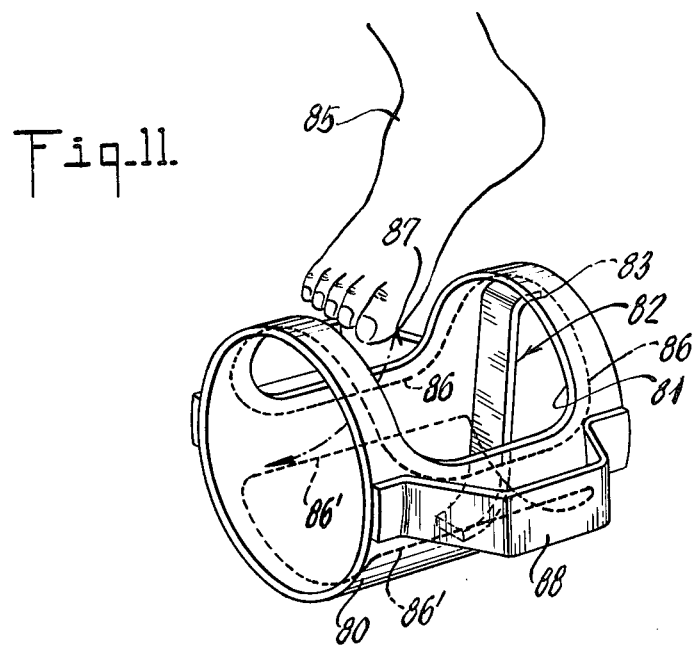
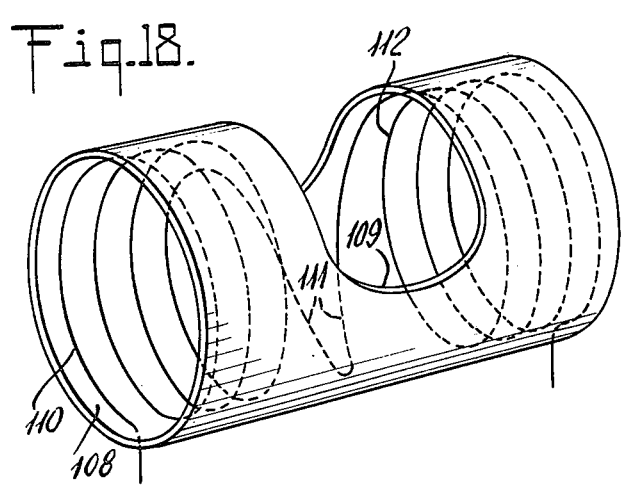
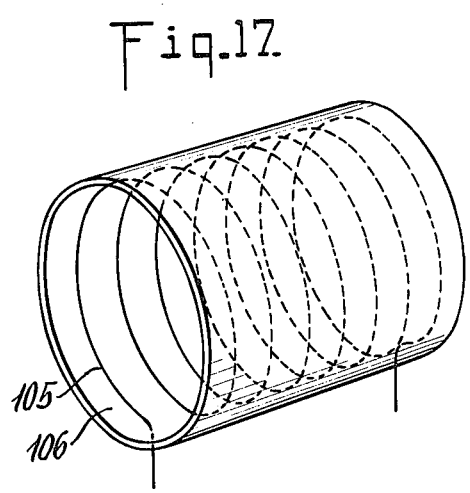
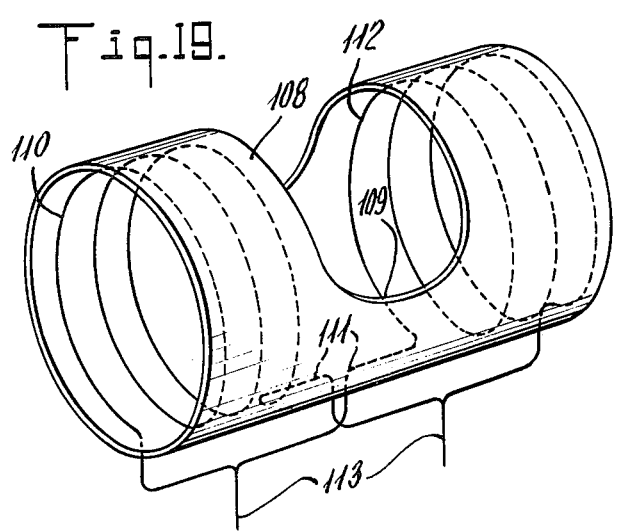
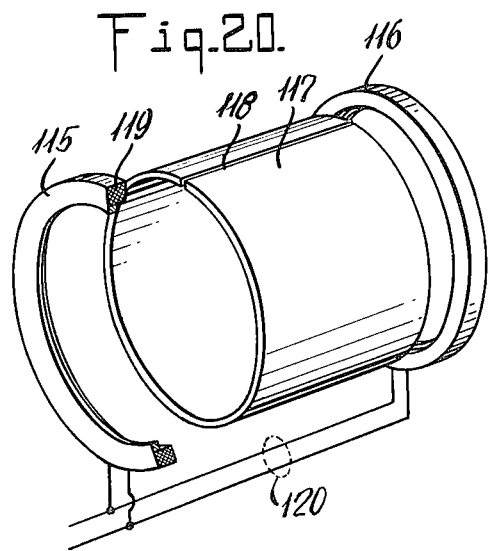

MODIFICATION OF THE GROWTH, REPAIR AND MAINTENANCE BEHAVIOR OF LIVING TISSUES AND CELLS BY A SPECIFIC AND SELECTIVE CHANGE IN ELECTRICAL ENVIRONMENT

CROSS-REFERENCE

This application is a continuation-in-part of pending application Ser. No. 742,706, filed Nov. 17, 1976 (now U.S. Pat. No. 4,105,017), and said pending application is a continuation-in-part of our original application Ser. No. 633,408, filed Nov. 19, 1975, entitled "Modification of the Behavior of Living Tissue and Cells by Electrical Means", said Ser. No. 633,408 being now abandoned.

BACKGROUND AND BRIEF DESCRIPTION OF THE INVENTION

This invention relates to the treatment of living tissues and/or cells by altering their interaction with the charged species in their environment. In particular, the invention relates to a controlled modification of cellular and/or tissue growth, repair and maintenance behavior by the application of encoded electrical information. Still more particularly, this invention provides for the application by a surgically non-invasive direct inductive coupling, of one or more electrical voltage and concomitant current signals conforming to a highly specific pattern.

Several attempts have been made in the past to elicit a response of living tissue to electrical signals.

Investigations have been conducted involving the use of direct current, alternating current, and pulsed signals of single and double polarity. Invasive treatments involving the use of implanted electrodes have been followed, as well as non-invasive techniques utilizing electrostatic and electromagnetic fields. Much of the prior work that has been done is described in Volume 238 of the *Annals of The New York Academy of Sciences* published Oct. 11, 1974 and entitled "Electrically Mediated Growth Mechanisms in Living Systems" (Editors A. R. Liboff and R. A. Rinaldi). See also "Augmentation of Bone Repair by Inductively Coupled Electromagnetic Fields" by C. Andrew L. Bassett, Robert J. Pawluk and Arthur A. Pilla published in Volume 184, pages 575–577 of *Science* (May 3, 1974).

The invention herein is based upon basic cellular studies and analyses which involve a detailed consideration of the interactions of charged species, such as divalent cations and hormones at a cell's interfaces and junctions.

Basically, it has been established that, by changing the electrical and/or electrochemical environment of a living cell and/or tissue, a modification, often a beneficial therapeutic effect, of the growth, repair and maintenance behavior of said tissue and/or cells can be achieved. This modification or effect is carried out by subjecting the desired area of tissues and/or cells to a specifically encoded electrical voltage and concomitant current, whereby the interactions of charged species at the cells' surfaces are modified. Such modifications engender a change in the state or function of the cell or tissue which may result in a beneficial influence on the treated site. For example, in the specific case of bone growth and repair, it is possible with one electrical code, hereinafter referred to as Mode 1, to change the interaction of the ion such as $Ca^{2+}$ with a cell's membranes. Whereas, with another electrical code, hereinafter referred to as Mode 2, a modification in the same cell's protein-synthesis capabilities can be affected.

For example, tissue-culture experiments involving the study of embryonic chick-limb rudiments show that the use of a Mode 1 code signal elicits enchanced $Ca^{2+}$ release of up to 50% from the competent osteogenic cell. This effect is highly specific to the parameters of the electrical code of Mode 1. Thus, this code influences one major step of ossification, i.e., the mineralization of a bone-growth site. Similar tissue-culture studies using Mode 2 code signals have demonstrated that this code is responsible for enhanced protein production from similar competent osteogenic cells. This latter effect is also highly specific to the parameters of the electrical code of Mode 2. In other words, this code affects certain metabolic processes for these types of cells such as those involved in calcium uptake or release from mitochrondria as well as the synthesis of collagen, a basic structural protein of bone.

These studies show that the electrical codes of Mode 1 and Mode 2 elicit individual tissue and cellular responses, indicating that each code contains a highly specific informational content therein. Based upon these and other studies, it has been possible to utilize Mode 1 or Mode 2 signals or a particular combination of Mode 1 and Mode 2 signals to achieve a specific response required to enable the functional healing of a bone disorder. These electrical modes have been applied successfully to human and animal patients for non-healing fractures such as congenital pseudarthrosis and non-unions as well as fresh fractures. Successes achieved in the congenital pseudarthrosis cases are particularly noteworthy, since normally 80% of children thus afflicted require amputation, since conventional treatments such as bone grafting and internal fixation are unsuccessful.

While there have been many investigations in the past of the response of living tissues and/or cells to electrical signals, clinical results to data using prior techniques have not been uniformly successful or generally accepted within the appropriate professional community. Several reasons contribute to this state. First, it has not been realized heretofore that electrical signals of very specific information content are required to achieve a specifically desired beneficial clinical effect on tissue and/or cells. Second, most of the prior techniques utilize implanted electrodes, which by virtue of unavoidable faradaic (electrolysis) effects are often more toxic than beneficial in the treated site. Furthermore, the cells and/or tissues are subjected to a highly uncontrolled current and/or voltage distribution, thereby compromising the ability of the cells to respond, should they do so, to the applied signal. This highly uncontrolled current and/or voltage distribution also applies in the case of capacitatively coupled signals.

In contrast, the surgically non-invasive direct inductive coupling of electrical informational content of specific electrical codes as involved in the present invention produces within living tissue and/or cells a controlled response.

In brief, the present invention involves the recognition that the growth, repair and maintenance behavior of living tissues and/or cells can be modified beneficially by the application thereto of a specific electrical information. This is achieved by applying pulse waveforms of voltage and concomitant current of specific time-frequency-amplitude relations to tissue and/or cells by a surgically non-invasive means through use of a varying electromagnetic field which is inductively coupled through direct induction into or upon the tissue and/or cells under treatment. The information furnished to the cells and/or tissues by these signals is designed to influence the behavior of non-excitable cells such as those involved in tissue growth, repair, and maintenance. These growth, repair and maintenance phenomena are substantially different from those involved in excitable cellular activity (e.g., nerves, muscles, etc.), particularly with respect to the type of perturbation required. Thus, the voltages and concomitant currents impressed on the cells and/or tissues are at least three orders of magnitude lower than those required to effect cellular activities such as cardiac pacing, bladder control, etc.

The invention will be more completely understood by reference to the following detailed description, in conjunction with the accompanying drawings, in which:

FIG. 1 is a simplified view showing the treatment of a bone in accordance with the invention;

FIG. 2 is a perspective view of the treatment unit shown in FIG. 1;

FIG. 3 is a view (from the rear) of the unit shown in FIG. 2, showing the positioning of a coil therein used for treatment purposes;

FIG. 4 is a block diagram of an electrical system for energizing the coil shown in FIG. 3 for Mode 1 treatment;

FIG. 5 is a block diagram of an electrical system for energizing the coil shown in FIG. 3 for Mode 2 treatment;

FIGS. 5a and 5b are pulse waveform diagrams for Mode 1 and Mode 2 treatments, respectively, showing presently preferred pulses as induced in living tissues and cells;

FIG. 6 shows alternative forms of negative pulse portions for Mode 2 treatment;

FIG. 7 is a front view of a body-treatment device, being an embodiment in substitution for that of FIG. 1, and shown unfolded, in readiness for wrapped application to an afflicted body region;

FIG. 7A is a sectional view, taken at 7A—7A of FIG. 7;

FIG. 8 is a perspective view of a locating element for use with the device of FIG. 7;

FIG. 9 is a simplified schematic illustration of a method of use of the device and element of FIGS. 7 and 8;

FIG. 10 is a simplified right-sectional view through a body-limb cast to which the device and element of FIGS. 7 and 8 have been applied;

FIGS. 11 and 12 are simplified views in perspective showing further body-treatment devices, for particular purposes;

FIGS. 17 to 20 are views similar to FIGS. 11 and 12 to show coil arrangements for further body treatment devices.

DETAILED DESCRIPTION

Figure 13:
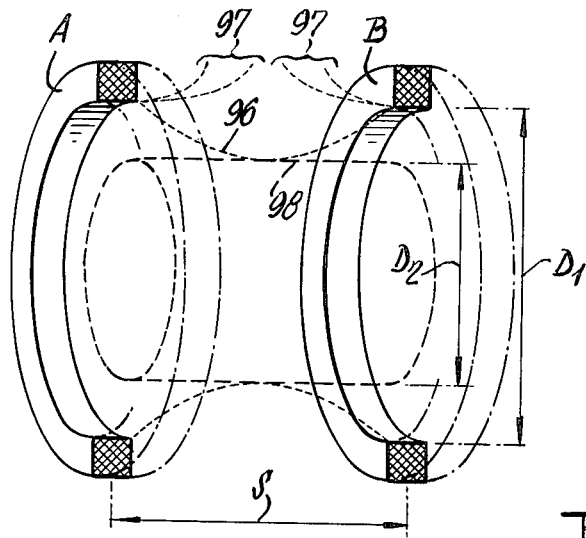
FIG. 13 is a diagram to illuminate discussion of dual-coil placement considerations.

Referring to FIGS. 1 to 3, the leg 10 of a person having a broken bone, as indicated as at 12, is shown as representative of the application of the invention to the stimulation of bone growth for healing purposes. A treatment head 14 is positioned outside the skin of the person, and is held in place by use of a strap 16 (secured to head 14 by fasteners 16a) which may include Velcro* material 18 thereon so that the strap may be wrapped about the leg and about the treatment head to maintain the treatment head in position against the leg. The treatment head 14 may include a foam material 20 on the inside surface thereof for the purpose of cushioning and ventilating the treatment head against the leg. It will be noted that the treatment head 14 is generally curved on the interior surface thereof so that it conforms to the shape of the leg under treatment.

*Velcro is a trademark of American Velcro, Inc., for its hook-and-loop fastener material.

The treatment head 14 includes therein a coil 22 which may be of any suitable shape. As shown in FIG. 3 the coil 22 is generally rectangular in shape so as to define a "window" within the interior portion of the turns of the coil. The coil 22 may lie in a plane or it may generally be curved to conform to the curvature of the treatment head 14. The coil 22 includes terminals 24 which extend away from the treatment head 14 to be coupled to a cable 26 for connection to a suitable energizing circuit, as will be explained below in more detail. A diode 27 may be included within the cable 26 for connection across the coil 22 as will also be explained below.

The treatment head 14 is positioned on the patient so that the "window" formed by the coil 22 is adjacent the break 12, i.e., adjacent the tissue under treatment. The coil 22 is energized, as will be explained in more detail below, and induces an electrical potential within the tissue under treatment. It has been found that a particular type of signal should be induced within the tissue and this is achieved by energizing the coil 22 by a circuit, such as shown in FIG. 4 or FIG. 5, to produce the pulse signal shown in FIG. 5a or FIG. 5b.

Referring to FIG. 4, a variable dc supply 30 is coupled through a gate 32 to the treatment coil 22 (or coils, as the case may be, and as will be explained in more detail below). The gate 32 is under the control of control units 34 and 36 which cause a pulse signal consisting of repetitive pulses of electrical potential to be applied to the treatment coil 22. Each pulse, as shown in FIG. 5a, is composed of a "positive" pulse portion P1 followed by "negative" pulse portion P2 because of the stored electrical energy within the treatment coil. In the circuit of FIG. 4, a diode clamping unit 38 may be employed to limit the peak potential of that negative pulse portion. The diode clamping unit 38 may be one or more diodes connected across the coil 22, and may be advantageously located within the cable 26. The diode 27 shown in FIG. 1 constitutes such a clamping unit 38.

In FIG. 5a, the signals at the treatment coil 22 and hence the induced signal within the tissue to be treated are shown. At time t1, it is assumed that gate 32 is gated on by an appropriate signal from control unit 36 (designated a pulse width control unit) so that the electrical potential across the treatment coil 22 is raised from about zero volts along pulse segment 39 to a potential designated v1 in FIG. 5a. The signal across the treatment coil decays in a second pulse segment along the portion of the curve designated 40 in FIG. 5a. The slope of that curve is determined by the L/R time constant of the circuit of FIG. 4, i.e., the inductance of the treatment coil and the effective resistance of the circuit, including distributed factors of capacitance, inductance and resistance. For treatment of many tissues and cells, it is believed desirable to adjust the circuit parameters so that the portion 40 of the curve is as flat as possible, rendering the signal applied to the treatment coil 22 as rectangular in shape as possible. At the time t2, the gate 32 is gated off by the control unit 36. Just prior to being gated off, the signal across the treatment coil is at the potential v2 shown in FIG. 5a. The potential across the treatment coil drops from the level v2 in a third pulse segment 41 to a potential of opposite polarity designated v3 in FIG. 5a. The magnitude of the opposite polarity potential v3 may be limited by the diode clamping unit 38 to a relatively small value as compared with value v1. The signal across the treatment coil 22 then decays from the potential level v3 to the zero or reference potential level, finally effectively reaching that level at time t3. A predetermined period passes before the pulse-repetition rate control unit 34 generates an appropriate timing signal to trigger the control unit 36 to generate a signal to turn gate 32 on again to continue the cycle just explained.

The control units may typically be monostable multivibrators, e.g., to generate appropriate timing signals and which may be variable to control pulse duration and repetition rate within desired limits. Further, the use of a variable dc supply 30 permits variation of the amplitude of the pulse signal as desired.

When pulse-train operation (Mode 2) is employed, additional timing circuitry similar to units 34 and 36 in FIG. 4 is employed to provide the burst-segment width and the burst-segment repetition rate. Referring to FIG. 5, control units 35 and 37 control gate 33 to produce a signal applied to coil(s) 22 of the waveform type as shown in FIG. 5b. The circuit is otherwise the same as in FIG. 4, except that the diode-clamping unit 38 is omitted to permit the large negative-pulse portions as shown in FIG. 5b. The control units 35 and 37 determine the number of pulses in a burst and the time between successive bursts.

It has been found that the signal across the treatment coil 22, and hence the induced signal within the tissue under treatment, should satisfy certain criteria. These criteria will be specified with respect to the signal as induced in the tissue and/or cells under treatment. Such induced signal may be monitored, if desired, by use of an auxiliary monitoring pickup coil (not shown) which is positioned at a distance from the treatment coil 22 corresponding to the distance of the tissue under treatment from that coil, as will be explained in more detail below. In any event, it has been found that the following criteria should be satisfied for effective treatment of living tissues and cells, in particular, hard tissue such as bone.

In the following presentation, the signals shown in FIGS. 5a and 5b constitute the pulses of electrical potential and concomitant current generated by the coil and impressed upon the tissues and/or cells. These pulses have one polarity upon "energization" of the coil (termed herein the "positive" pulse portion and shown as the positive-going portion of the waveform on FIGS. 5a and 5b). These pulses have an opposite polarity upon "de-energization" of the coil (termed herein the "negative" pulse portion and shown as the negative-going portion of the waveforms of FIGS. 5a and 5b). The terms "positive" and "negative" are intended to be relative only, and are used herein only for the purpose of indicating that pulse portions of opposite polarity, with respect to a reference potential level, are involved.

It has been determined that the "positive" pulse portions should bear a predetermined relationship to the "negative" pulse portions in order to modify beneficially and with uniform results the behavior of living tissues and cells. This predetermined relationship has been achieved by the utilization of two different signal modes, as well as combinations thereof.

In Mode 1 (see FIG. 5a), the asymmetrical waveform induced in tissue or cells by the alternate energization and de-energization of an electromagnetic coil is repeated at a frequency such that the overall duty cycle is no less than about 2%. This frequency, in Mode 1, has typically been about 10–100 Hz with duty cycles of 20–30%. The basic relationship for Mode 1 of the respective frequency amplitude content of the "positive" and "negative" pulse portions is as follows: pulse signal should be of a particular shape, namely, each "positive" pulse portion should be composed of at least three segments, e.g., the segments 39, 40 and 41 in FIG. 5a. As noted above, it has been found that a substantially rectangular shaped "positive" pulse signal portion is particularly useful in the treatment of tissue and cells. However, it is possible that other pulse configurations (other than a simple two-segment spike) may be useful. The peak amplitude of the final segment of each "positive" pulse portion, e.g., the potential v2 in FIG. 5a should be no less than about 25% of the peak amplitude of the first segment 39 of the "positive" pulse portion, e.g., the potential v1 in FIG. 5a.

The peak "negative" portion amplitude is denoted by v3 in FIG. 5a. This peak amplitude should be no more than about ⅓ the peak amplitude of the "positive" pulse portion. The time duration of each "positive" pulse portion (the period that elapses between times t1 and t2 in FIG. 5a) should be no longer than about 1/9 the time duration of the following "negative" pulse portion (the time elapsing between times t2 and t3 in FIG. 5a). Because the treatment system utilizes an electromagnetic coil, the energy of each "positive" pulse portion is equal to the energy of each "negative" pulse portion, i.e., the area in FIG. 5a embraced by the "positive" pulse portions is equal to the area embraced by the "negative" pulse portions. By satisfying the criteria just mentioned, the energy of each "negative" pulse portion is dissipated over a relatively long period of time, and the average amplitude of that negative pulse portion is limited. It has been found that such average negative amplitude should be no greater than about 1/6 the average amplitude of the "positive" pulse portion.

These relationships also ensure that the "positive" and "negative" pulse portions have the proper frequency-amplitude characteristics within themselves and to each other such that a beneficial modification of the behavior of tissues and cells is accomplished.

Besides the relationships just mentioned, it has been found that the average magnitude of the "positive" pulse portion peak potential should be within the range of about 0.0001 to 0.01 volt per centimeter of tissue or cells, corresponding to between about 0.1 and 10 microampere per square centimeter of treated tissue and/or cells (based upon typical cell and tissue resistivities). It has been found that higher or lower pulse potentials will not result in a beneficial effect. It has also been found that the duration of each "positive" pulse portion (the time elapsed between times t1 and t2 in FIG. 5a) should be at least about 200 microseconds. If the time duration of each "positive" pulse portion is less than about 200 microseconds, the tissues and cells are not stimulated sufficiently to modify the repair or other processes. From a practical standpoint, the "positive" pulse portion duration should not be greater than about 1 millisecond. It has also been found that the repetition rate of the pulses should be within the range of about 65 to 75 Hz for bone and other hard tissues. Pulse treatments within this range have been found to be particularly effective with reproducible results for tissues and cells of this type. In general, however, pulse repetition rate should be between about 10 and 100 Hz for good results in tissues and cells.

For the treatment of bone disorders, and particularly for the treatment of pseudarthrosis, it has been found that for Mode 1 an optimum induced "positive" pulse signal portion having a peak amplitude of between about 1 and 3 millivolts per centimeter of treated tissue (1 to 3 microamperes per square centimeter of treated tissue and/or cells) with the duration of each "positive" pulse portion being about 300 microseconds and the duration of each of the "negative" pulse portions about 3300 microseconds, and a pulse repetition rate of about 72 Hz, represents a presently preferred and optimum induced pulse treatment as long as the pulse-shape requirements noted above are met. Total treatment times may vary. It is presently believed that pulse-signal treatments for periods each lasting for at least about 15 minutes, with one or more periods of treatment during a prescribed number of days, may be effective in stimulating tissue and cell behavior. A preferred treatment regime using Mode 1 has been found to be a minimum of 8 hrs/day for a period of four months in difficult cases, and two weeks in less difficult cases.

In Mode 2 treatment (FIG. 5b), the asymmetrical waveform induced in tissue or cells by the alternate energization and de-energization of an electromagnetic coil is applied in a pulse-train modality, which contains bursts (pulse groups) of asymmetrical waveforms. Each burst of asymmetrical pulses has a duration such that the duty cycle of the burst portion is no less than about 1%. The burst frequency has typically been about from 5–50 Hz.

The basic relationships for Mode 2 of the respective frequency-amplitude content of the "positive" and "negative" pulses within the burst section of the pulse train are as follows: each "positive" pulse portion should be composed of at least three segments, e.g., the segments 39', 40' and 41' in FIG. 5b. For this mode, it has also been found that a substantially rectangular shaped "positive" pulse-signal portion is particularly useful in the treatment of tissues and cells. However, it is possible that pulse configurations other than a simple two segment spike may be useful. The peak amplitude of the final segment of each "positive" pulse portion, e.g., the potential $v_2$ in FIG. 5b, should be no less than about 25% of the peak amplitude of the first segment 39' of the "positive" pulse portion, e.g., the potential $v_1$ in FIG. 5b.

The peak "negative" amplitude is denoted by $v_3$ in FIG. 5b. This "negative" peak amplitude should be no more than about 40 times the "positive" peak amplitude (in this case v1). This requirement may be met by utilizing "negative" pulse portions having several different waveshape forms, e.g., substantially rectangular, trapezoidal with exponential decay, bell-shaped, or single-spike with exponential decay, as in representative waveforms a, b, c and d in FIG. 6.

The duration of each "positive" pulse portion (the time that elapses between times t1 and t2 in FIG. 5b) should be at least about 4 times the duration of the following "negative" pulse portion (the time that elapses between times t2 and t3 in FIG. 5b). As noted above, since the treatment system utilizes an electromagnetic coil, the energy of each "positive" pulse portion is equal to the energy of each "negative" pulse portion, i.e., the area in FIG. 5b embraced by the "positive" pulse portions is equal to the area embraced by the "negative" pulse portions.

The pulse-repetition rate of the pulses within the burst segment of the Mode 2 pulse train (the time elapsing between times t1 and t4) can be between about 2000 Hz and 10,000 Hz.

The width of the burst segment of the pulse train (the time elapsed between t1 and t5) should be at least about 1% of the time elapsed between t1 and t6.

By satisfying the criteria just mentioned, these relationships also ensure that the "positive" and "negative" pulse portions have the proper frequency-amplitude characteristics within themselves and to each other such that a beneficial modification of the behavior of tissues and cells is accomplished.

Besides the relationships just mentioned, it has also been found that the average magnitude of the "positive" peak potential should be within the range of about 0.00001 to 0.01 volts per centimeter of tissues and/or cells (between about 0.01 and 10 microampere per square centimeter of treated tissue and/or cells).

It has been found that higher or lower pulse potentials will not result in a beneficial effect on tissues and/or cells. It has also been found that the duration of each "positive" pulse portion in the burst segment of the pulse train (i.e., the time elapsed between t1 and t2 in FIG. 5b) should be at least about 1000 microseconds. It has also been found that the repetition rate of the burst segment should be within the range of about 5–15 Hz for bone and other hard tissues.

Each negative-pulse portion within the burst segment of the pulse train should be of a duration no greater than about 50 microseconds and of an average amplitude no greater than about 50 mv/cm of treated tissue and/or cells (about 50 microamperes per square centimeter of treated tissue and/or cells).

For the treatment of bone disorders, and particularly for the treatment of pseudarthroses and non-unions, it has been found that an optimum induced "positive" pulse signal portion having a peak amplitude of between about 1 and 3 millivolts/centimeter of treated tissue (i.e., 1 to 3 microamperes per square centimeter of treated tissue and/or cells), with the duration of each "positive" pulse portion being about 200 microseconds, and the duration of each of the "negative" pulse portions being about 30 microseconds, and a time elapsed between times t3 and t4 of FIG. 5b of 10 microseconds, and a pulse repetition rate of about 4000 Hz, and a burst segment width of about 5 milliseconds, and a burst repetition rate of about 10 Hz, represents a presently preferred and optimum induced pulse treatment in bone for Mode 2, as long as the pulse requirements noted above are met.

It is also believed that a single asymmetrical pulse as described in the burst segment of Mode 2 can be employed at a repetition rate similar to that used in Mode 1 for beneficial modification of tissue growth and repair.

Treatment of living tissues and cells by the above methods herein, in particular for hard tissue such as bone, has demonstrated an increased repair response and generally uniform results have been attained throughout all patient and animal treatments. Particularly beneficial results have been obtained in the cases of treatment of pseudarthrosis in which a bone union has been achieved following previous unsuccessful attempts by other treatment methods and in which amputation has been discussed as a possible alternative to regain function.

In practice, it is believed desirable to utilize as large a coil "window" as possible and to position the coil such that an adequate flux density is impressed upon the tissue and/or cells being treated. As is known, a time-varying magnetic field induces a time-varying voltage field orthogonal to it. That is, the geometry of the magnetic-field lines determines the geometry of the induced-voltage field. Because a relatively uniform induced-voltage field is desired, the geometry of the magnetic-field lines should be as uniform as possible, which may be achieved by rendering the size of the coil relatively large with respect to the area under treatment. At this particular time, it is not believed that there need be a particular orientation between the magnetic-field lines and the tissue and/or cells being treated.

It is believed that the uniformity of the induced-voltage field possible through electromagnetic treatment is responsible in many respects for the good treatment results which have been obtained, in distinction to the non-uniform fields which may and probably do result with other types of treatments, for example, utilizing electrostatic fields or by the creation of a potential gradient through the use of electrodes implanted within or on tissues or cells. In particular, an induced voltage field is present in a vacuum as well as in a conducting medium or an insulator. The field characteristics will in general be the same (within one percent) in these three cases, except in the case for which an induced current flow is sufficiently great to create a back electromotive force to distort the magnetic field lines. This condition occurs when the conducting medium has a high conductivity, e.g., a metal, and is large enough to intercept a substantial number of magnetic-field lines. Living systems, i.e., tissue and/or cells, are much less of a conductor than a typical metal (generally by at least $10^5$ i.e. five orders of magnitude). Because of these considerations, the geometry of the magnetic field present in tissue and/or cells is undisturbed and remains unchanged as the tissue and/or cell growth process continues. Thus, with non-invasive electromagnetic treatment, it is believed that the potential gradient that is produced within the tissue and/or cells is constant regardless of the stage or condition of the treatment.

Such uniformity of induced potential is virtually impossible to be achieved through the use of implanted electrodes or by an electrostatic coupling or by a transformer coupled to electrodes, or by implanted coils coupled to electrodes. Since these latter types of treatments are dependent upon conductivity, which will vary within tissue and/or cells, the induced potential gradient will not be constant as the condition of the tissue and/or cells changes. Additionally, at any particular time within tissue and/or cells, individual localities of the material being treated will have different conductivity characteristics, which will result in differing potential gradients throughout the material treated.

For these reasons, it is believed that a surgically non-invasive electromagnetic treatment of tissue and/or cells is greatly preferable to electrical treatment by other means.

Regarding typical coil parameters, it is believed that for typical bone breaks, coil windows of about 2.0"×2.75" (for an adult) and 2"×1.5" (for a child) are suitable. The wire employed in the coils may be B&S gauge 12 copper wire that is varnish-coated to insulate the turns one from another. Coils of about 60 turns for an adult and 70 turns for a child seem to be suitable. For treatments in the oral cavity, coil sizes would be correspondingly smaller.

It is believed that the inductance of the treatment coil should be between about 1–5000 microhenries, and preferably between about 1000 and 3000 microhenries, with sufficiently low resistance (e.g., $10^{-2}$ to 1 ohm) and a high input coil driving signal between about 2 and 30 volts, to induce the appropriate pulse potential in the tissue and/or cells treated. The lesser the inductance of the treatment coil, the steeper the slope of the curves 40 and 40' as shown in FIGS. 5a and 5b; the greater the inductance, the flatter or more rectangular is the "positive" pulse that is produced.

The monitoring of the induced potential may be by actual electrodes making contact with the tissue and/or cells being treated or by use of a pickup coil positioned adjacent to the treatment coil 22 at a distance corresponding to the distance of the material under treatment from the coil. A typical pickup coil that has been employed is circular, about one-half centimeter in diameter, with about 67 to 68 turns of wire. The potential developed by the coil is divided by the length of the wire (in centimeters) to provide an induced voltage per centimeter number that is closely related to the volts per centimeter induced in the tissue and/or cells under treatment.

A typical treatment utilizing a coil having a "window" 2"×2.75" and 60 turns of number 17 gauge wire, including a diode at the coil such as the diode 27 in FIG. 1, produced the following induced voltages in a pickup coil* for the pulse times (in microseconds) as follows (voltages and times are with reference to the waveform of FIG. 5):

*These voltage values may be translated into millivolts per centimeter of tissue, by dividing by a factor of substantially ten.

| Induced Voltage | v1 | v2 | v3 | t1–t2 | t2–t3 |
|---|---|---|---|---|---|
| Maximum (at face of treatment coil) | 22 | 17 | 3.7 | 300 | 4200 |
| ⅜" from face of treatment coil | 15 | 11.5 | 2.5 | 300 | 4200 |
| 1½" from face of treatment coil | 6.0 | 4.2 | 1.0 | 300 | 4200 |

The use of pulsing electromagnetic fields to control bone formation in a variety of conditions, now, is on a sound experimental and clinical basis. Thus far, the developments have had application in treating successfully congenital and acquired pseudarthrosis and fresh fractures in humans, increasing the rate of fracture and reactive periostitis repair in animals, and reducing bone loss in dis-use osteoporosis of long bones. Success with the method hinges on the discovery of pulse patterns with specific time-frequency-amplitude relationships as outlined above.

EXAMPLES

In order to demonstrate efficacy, the utilization of direct inductive coupling of electromagnetically induced pulsing voltages and concomitant current via Modes 1 and 2 and combinations thereof for hard tissue growth and repair was initially applied in cases of congenital and acquired pseudarthrosis. In a group of patients, only individuals who had been treated previously by one or more unsuccessful surgical attempts (grafting, internal fixation) were accepted. For most of these patients, amputation had been recommended by at least one qualified orthopedist. Throughout this study, the necessity for pulse specificity was illustrated again and again. For example, when lack of ossification was the primary problem (usually the case for congenital pseudarthroses), Mode 1 treatment was utilized with final functional bony union occurring *only* when the parameters of the pulse corresponded to those given above. On the other hand, when lack of bony matrix was the primary problem, Mode 2 treatment was employed in order to achieve the production of collagen which is the primary supporting protein in bone structure. Since protein production and ossification are two completely different steps in bone formation, the highly selective nature of each of the signals utilized in Modes 1 and 2 could be synergistically combined when neither matrix production nor ossification were present in a given patient's treatment history. Thus, a combination of Modes 1 and 2 was utilized with benefit in this type of situation.

In the case of congenital pseudarthroses, the typical patient is between one and ten years of age. The afflicted part is normally the distal tibia of one extremity. The patients were presented with an average of three prior unsuccessful surgical procedures and had the condition for an average of 5 years, and all were candidates for amputation.

The treatment of such a patient was normally carried out using Mode 1 treatment regime since the primary problem was due to a lack of ossification in the affected area.

The patient is prescribed the appropriate equipment by the attending orthopedic surgeon and carries out his treatment on an out-patient basis. Treatment time is typically 12 to 16 hours a day for about an average of 4 months.

Some 20 of this type of disorder have been treated to date with successful ossification achieved in approximately 90% of the treated individuals.

For acquired pseudarthrosis, either traumatic or operative, patients are mostly adults and had an average number of three failed operations and an average of 2.5 years from onset of non-union. Amputation had been discussed for seventy percent of these individuals. Since in some cases the primary problem was lack of bony matrix, typically visible radiographically as gaps in the bone of more than 2 mm in the fracture site, such a patient was treated commencing with Mode 2 modality. When it was thought that sufficient non-ossified bony matrix was present, Mode 1 modality was employed to gain rapid immobilization of the fracture site.

Because of the particular pathology of several patients in this group, a combination of Modes 1 and 2 was employed with this treatment being specifically Mode 2 followed by Mode 1. As in the case of congenital pseudarthrosis, the proper equipment was prescribed by the attending orthopedic surgeon and treatment was performed on an out-patient basis. Treatment time is typically 10–14 hours/day for periods ranging from 3 to 9 months.

Some 30 of this type of disorder have been treated to date with successful bony union observed in 75% of the treated individuals.

These clinical results clearly demonstrate that once the particular pathology of a bone disorder is diagnosed it can be selectively beneficially treated by the application of properly encoded changes in electrical environment.

Similar findings have been obtained from a study of bilateral fermoral and radial osteotomies in 160 rats. These animals were divided into two major groups; field exposed and control for an interval of 14 days after operation. Following sacrifice, the extent of fracture repair was judged on the basis of X-ray and histologic evaluation, coupled with non-destructive mechanical testing. These animal models were employed to evaluate the effectiveness of treatment modalities of Modes 1 and 2 and combinations thereof. Generally, when the osteotomy gap was less than 1.0 mm, a Mode 1 signal was effective since very little bony matrix was required for solidification. On the other hand, for wider osteotomies, substantially increased matrix production was observed over control animals when Mode 2 was employed. A combination of Modes 1 and 2 was employed in the latter case to obtain a stiffer repair site for an equivalent treatment time.

This was further evaluated by the response of these bones to mechanical testing. This was performed by subjecting the bone of the rats following sacrifice to cantilever loading at various deformations in accordance with the testing procedures described in "Acceleration of Fracture Repair by Electromagnetic Fields. A Surgically Non-invasive Method" by C. A. L. Bassett, R. J. Pawluk and A. A. Pilla, published on pp. 242–262 of the *Annals of The New York Academy of Sciences* referenced above. The specimens were deformed in the antero-posterior, lateral-medial, postero-anterior, medial-lateral and again the antero-posterior positions.

The average response of a femur to this test at a deformation of 0.05 inch is shown in Table I as follows:

TABLE I

Mechanical Load Values In Electrical Stimulation of Artificial Osteotomies In Adult Female Rat Femur

| Stimulation | Load at 0.05 in. Deformation |
| --- | --- |
| Control (untreated) | 42 gms. ± 5.2 gms. |
| Mode 1 Signal (FIG. 5a) | 580 gms. ± 65 gms. |

In addition to radiographic and mechanical evidence of the effectiveness of the signal employed, histologic evidence further attests to this effectiveness.

Hemotoxylin and eosin stained longitudinal specimens show a much higher degree of maturation for the Mode 1 signal than in the control case.

For wider osteotomy gaps, treatment times of fourteen days showed that the active animals had a significantly larger callus than controls. Histologic evidence shows that the increase is at least 150% over controls.

Limited tooth extraction studies have been performed and show that pulses of the Mode 1 type may have a highly beneficial effect on the rate of healing and on bone loss in the oral cavity. The latter effect in the oral cavity is particularly important for the maintenance of mandibular and maxillar crestal bone height, a very important factor for implant fixation.

These observations all point to the fact that electromagnetic fields with highly specific pulse characteristics can be non-invasively inductively coupled to biological systems to control cell behavior. In the initial application of these principles, effects on bone cells have been investigated. Other biological processes, however, may eventually be proven to be controlled by similar techniques, e.g., malignancy, neuro-repair, inflammatory processes and immune response, among others.

In summary, it is believed that a unique electromagnetic and surgically non-invasive treatment technique has been discovered. Induced pulse characteristics appear to be highly significant, especially those relating to the time-frequency-amplitude relationships of the entire pulse or pulse sequence. It is believed that selection of particular time-frequency-amplitude relationships may be the key to successful treatments of varying cellular behavior in a variety of tissues.

Throughout the specification for Mode 1, a preferred pulse repetition rate of between about 65 and 75 Hertz had been specified for bone and other hard tissue. The exact limits of the pulse-repetition rate are not known for all types of tissues and cells. It is believed that preferred operating ranges will vary depending on the tissue and cell type. Positive results have been obtained, for example, in soft-tissue treatment at 20 Hertz.

It will be appreciated that the methods and apparatus described above are susceptible of modification. For example, while FIGS. 1 and 2 illustrate a treatment unit which may be strapped to the leg, treatment units incorporated in casts, e.g., may be employed. Further, treatment may be carried out by use of one or more coils of varying shapes positioned adjacent to tissue and/or cells to be treated. In fact, some treatments of humans have involved coils positioned upon opposite sides of a bone break. Coils with metal cores may also be used. In the case of treatment within the oral cavity, it is believed that double coils are advantageous, positioned, for example, on opposite sides of a tooth socket to stimulate repair of that socket. Some specifically beneficial treatment units and procedures will be described in connection with FIGS. 7 to 16.

FIGS. 7 and 7A illustrate a body-treatment or applicator device which is most beneficial applied to the treatment of bone breaks or non-unions in arm or leg members, i.e., wherein the bone region to be treated is relatively elongate. The device comprises two coil-mounting units 50-51 each of which contains an electrical coil of the character already described, and they are flexibly interconnected to permit ready adaptability to opposite sides of the region to be treated. Each of the units 50-51 may be of like construction, essentially involving a rigid potting of its coil turns in a consolidating mass of cured elastomeric or plastic material; however, in the preferred form, each unit, such as unit 50, comprises a casing consisting of flanged concave-front and convex-back panels 52-53, with the peripheral flange 54 of front panel 52 in continuous telescoping overlap to the similar flange 55 of back panel 53. Registering and abutting inwardly projecting boss or foot formations in panels 52-53, as at 56, enable the two panels to be bolted together in the precisely spaced relation shown in FIG. 7A. The respective inner and outer panels of unit 51 are precisely the same as for unit 50, except that as a further feature of the invention a rectangular recess 57 is inwardly formed in panel 52, for a locating or key purpose to be later explained. The secured boss or foot formations at 56 are preferably offset inwardly from the flanged peripheries of panels 52-53, thereby defining peripherally spaced means for locating the inner limit of turns of coil 58 within the flange 55 of back panel 53. The coil turns may be rigidly bonded in place, to and within flange 55, or they may be adequately retained by compressible material such as urethane foam, compressed as the bolted connections are established at 56.

The flexible interconnection of units 50-51 is shown to include an electrical cable 59 for establishing the electrically parallel interconnection of like coils 58 in the respective units 50-51, the polarity of such interconnection being such that magnetic-flux lines within the two coils 58 and in the space therebetween are flux-adding when the front (concave) panels of units 50-51 are in face-to-face relation. Removable connection of the coils 58 to the energizing circuitry of FIG. 4 or 5 is shown by way of the single plug and socket means 24–26, via unit 51. Typically, each of the two coils 58 has an inductance in the order of 5000 microhenries, so that in their preferred parallel relation the inductance presented to the output of the applicable one of the circuits of FIGS. 4 and 5 is 2500 microhenries.

The flexible interconnection of units 50-51 also includes articulating strap means, as of Velcro material, to enable simple adaptation to the dimensional requirements of each patient's particular circumstances. Thus, unit 50 is shown with a first such strap element 60 secured to its back panel 53 and having a free end extending a distance $L_1$ to one lateral side of unit 50; similarly, unit 51 is shown with another strap element fixed to its back panel and having a first free end 61 of length $L_1$ extending laterally for adjustable overlapping connection to the free end of strap 60. The opposite end 62 of the strap carried by unit 51 is also free but of substantially greater length $L_2$, to permit full circumferential completion of the strap connection as the means of removably applying both units 50-51 to the body-member treatment region; preferably, the length $L_2$ is sufficient to enable the velcro-material region 63 at the inner or front face of the free end 62 to circumferentially envelop the body member and to enable region 63 to have removable Velcro engagement with a suitably equipped back surface of the same strap member, as at the region of its fixed mounting to the back panel of unit 51.

The coils 58 are shown to be of generally elliptical configuration. These coils should be of sufficiently large internal dimensions, in relation to their ultimately installed positioning for bone treatment, as to assure relatively uniformly distributed concentrated flux within the treatment zone. Elementary principles and preferred dimensional relationships for a two-coil flux-aiding circular configuration will be later discussed, with a view to minimizing the establishment of stray-flux lines between the two coils. It suffices here to point out that by employing the cylindrically concave-convex configurations described for panels 52-53, the coils 58 are necessarily also conformed to a geometrical shape which is cylindrically arcuate, the major-axis direction of the ellipse being parallel to the axis about which each coil 58 is cylindrically arcuate. Thus, when units 50-51 are positioned for body treatment, the concave sides of both coils 58 are in face-in-face relation, with the minor-axis spaced coil regions m-n of unit 50 in closer adjacency to the corresponding minor-axis spaced coil regions m'-n' of unit 50 than is the case for coil-to-coil spacing of corresponding major-axis spaced coil regions p-q and p'-q'; as a result of this relation, any tendency to establish stray-flux lines between corresponding minor-axis coil regions m-n' and m'-n is minimized.

Specific use of the body-treatment device of FIGS. 7 and 7A will be more clearly understood through additional reference to FIGS. 9 and 10, utilizing a locating-block or keying device (shown in FIG. 8) which may be expendable and of suitable molded plastic such as polypropylene. The locating device of FIG. 8 comprises a rectangular-prismatic block 65 which is dimensioned for removable locating reception in the rectangular recess formation 57 that is central to the concave panel 52 of unit 50. Integrally formed with and extending in opposite longitudinal directions from the base of prism 65 are elongate mounting strips 66 which are relatively stiffly compliant for slight bending adaptation to particular body or cast configurations. Also, the thickness and material of strips 66 should be such as to permit sheared cut off to shorter length, as may be needed for some applications. A pressure-sensitive tape 67, which may incorporate metal foil, wire or other material opaque to radiological irradiation is shown to be removably adhered to the peripheral edge of block 65.

In the initial stages of use of the device of FIG. 7, i.e., during the period in which the separate halves of a bone break or non-union are to be fixedly retained for electromagnetically induced treatment of the invention, the afflicted limb, for example, the leg 70 of FIG. 9, is first placed in a cast 71 which overlaps the afflicted region. The leg is then placed on a table 72 so that the afflicted region can be viewed under radiological irradiation, schematically designated by an arrow, with the legend "X-Rays", instantaneous and current viewing being provided by suitable video-scanning and display means 73-74. The device of FIG. 8 is then placed upon a local region of the cast 71 such that the opaque periphery of prism 65 is viewable at 74 as a rectangular frame, surrounding the central zone of the bone-break or non-union region to be treated. When the opaque frame is seen in the display in proper surrounding registry with the afflicted bone region, i.e., after such positioning adjustments as may be needed to assure such registry, the strip ends 66 are fastened to the cast 71, as by means of adhesive tape suggested at 68. The cast 71 may then be further developed over the strip ends 66 to assure permanence of the locating prism as a fixed part of cast 71. When prism 65 is thus fixed to cast 71, strip 67 may be removed and discarded, and the patient is ready for the device, of FIG. 7, which is assembled by first locating (i.e., keying) unit 50 via recess 57 to the prism 65, by then adjusting the velcro overlap 60-61 to position unit 51 in diametrically opposite relation to unit 50 (on the other side of cast 71), and by then using the strap end 62 for completion and securing of the circumferential overlap described for the inner-surface region 63. The electrical connection is then completed at 24-26, and treatment may commence in the manner already described. It should be noted that, if the surface of the concave panel of each unit 50-51 is not soft-textured, there may be a tendency to generate chalk dust upon local mechanical fretting of the cast 71, with repeated assembly and disassembly of units 50-51 thereto. Such fretting can be minimized by adhering a foamed-plastic or the like yieldable liner to the concave panel of one or both units 50-51, such a liner being shown at 75 in FIG. 10. Still further, the use of a foamed-plastic liner will assure greater patient comfort while frictionally contributing to stable placement and retention of the treatment coils.

FIG. 11 depicts a body-treatment device which is particularly suited to the treatment of bone afflication in the region of the heel. For simplicity in FIG. 11, the showing is limited to relatively rigid structural components, and the foamed-plastic lining carried by such structure for patient comfort (i.e., to avoid chafing) has been omitted. Basically, the rigid structure of FIG. 11 comprises a tubular shell 80, as of methylmethacrilate, being open at its longitudinal ends and locally open at 81, over an angular span (about the shell axis) and intermediate the longitudinal ends of shell 80. An "S"-shaped strap 82, which may be of the same material as shell 80, has its upper end secured at 83 to the back end of shell 80, at opening 81, and its lower end 84 extends along the diametrically opposite region of the inner surface of shell 80, to define a plate for basic support of the bottom of a foot 85, to be inserted via the opening 81. The respective courses of two arcuately curved elliptical coils 86-86' are schematically indicated by heavy dashed lines. These coils will be understood to be bonded to shell 80 in vertically opposed relation, the upper coil 86 being bonded to the inner surface of shell 80, just inside the edge of opening 81, and the lower coil 86' being similarly bonded at the diametrically opposite location. Coils 86-86' thus have a permanent relation to each other, much the same as described for the coils 58 of units 50-51, once the latter are in body-assembled relation; and it will be understood that coils 86-86' are preferably electrically connected in parallel, in flux-aiding polarity, being excited by one or the other of the energizing circuits of FIGS. 4 and 5.

In addition to the described coil-positioning and foot-supporting structure, the device of FIG. 11 includes side-bumper guards 87-88 which may be bowed strips of the same plastic material as shell 80, suitably bonded at both ends to the respective longitudinal ends of shell 80. Strips 87-88 are preferably stiffly yieldable, to cushion the treated region from mechanical shock in the event of unwitting contact with furniture or other objects.

Figure 12:
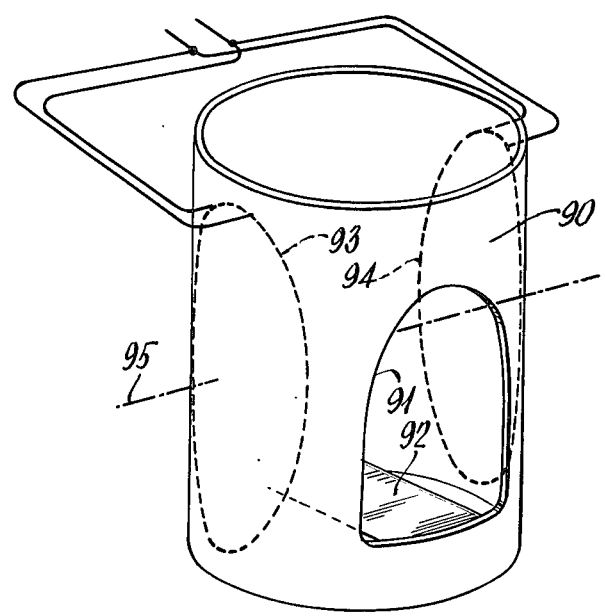

FIG. 12 is a simplified diagram similar to FIG. 11 to illustrate another body-treatment device, configurated for application to an afflicted ankle region, or to a lower tibia/femur region. Again, the basic rigid structure is seen to comprise a tubular shell 90, as of suitable plastic. A single local side-wall opening 91 in shell 90 has a straight lower edge, contiguous to a bottom plate or rest 92 which diametrically spans the lower end of shell 90. Opposed electrical coils 93-94 are bonded to the inner surface of shell 90 at an elevation such that the alignment 95 to their centers of symmetry will geometrically intersect the center of the afflicted region, preferably as confirmed by X-ray observation on the alignment 95. The configuration of coils 93-94 may be circular or elliptical, but is preferably cylindrically arcuate, in conformance with the local shell surface to which each of them is bonded; in the event of elliptical coil configurations, the major-axis orientation is preferably vertical, consistent with the discussion above as to coils 58 in FIG. 7. Interconnection and excitation of coils 93-94 is as described for other two-coil devices.

It will be seen that the described devices and techniques represent major advances in surgically non-invasive treatment of body cells, particularly as they may be involved in bone repair and healing. With respect to the body-treatment devices which have been described, we have not yet established the full range of dimensional limitations, but certain beneficial ranges can be described in general terms, particularly for dual-coil embodiments, illustratively disclosed in connection with FIGS. 7 to 12.

On an elemental basis, it is convenient to consider the circular-coil situation depicted in FIG. 13, wherein like circular coils A-B of inside diameter $D_1$ are positioned on a common central axis of symmetry, at parallel planes which are spaced apart by the distance S, and wherein the coils A-B are excited in flux-aiding relation. If the spacing S is sufficiently small in relation to the diameter $D_1$, then substantially all flux lines within coils A-B will extend continuously therebetween, on a generally straight alignment which may even neck down as suggested by the profile 96. If the spacing S is greater (again in relation to the diameter $D_1$), some stray-flux lines 97 will develop, to the detriment of the development of uniform high-density flux in the central span S. Generally, in view of the necking down (96), and in view of the treatment zone being generally at the center of span S, it is convenient to consider the coils A-B is being desirably effective in producing the uniform flux distribution over an imaginary cylinder 98 of diameter $D_2$, tangent to the neck-down profile 96. From our experience to date, we can state that for body application of the character presently described, the span S should be equal to or less than the diameter $D_1$, and of course $D_2$ (the effective diameter of the zone of body treatment) will always be considerably less than $D_1$, being substantially equal to $D_1$ only when coils A-B are closely adjacent. As a practical consideration in the application of dual coils to the body, we consider that the nominal inside diameter $D_1$ of the coils should be at least 1.5 times the diameter $D_2$ of the effective body-treatment zone, and this has been found to be a reliable approach for coil spacing S substantially equal to the inside diameter $D_1$.

Figure 14:
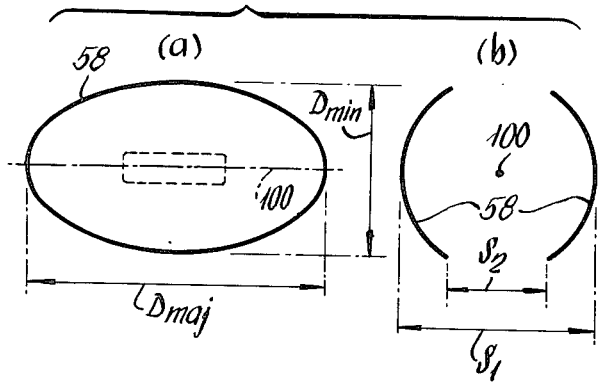
FIGS. 14, 15 and 16 are similar pairs of views a and b, respectively schematically representing front and side elevational views for each of three different generally elliptical dual-coil configurations.
Figure 15:
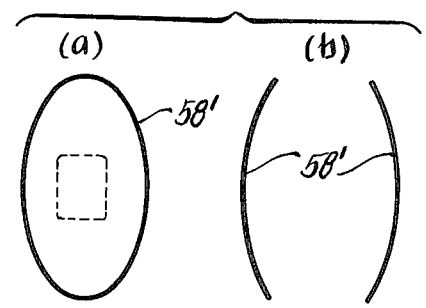

Having thus considered criteria factors for the simplified case of flat circular coils, it is possible to develop general criteria applicable to elliptical coils which are "wrapped" in general conformance with a cylindrical arc. FIG. 14 schematically depicts the coil-58 relationship discussed for FIG. 7, wherein the cylindrical arc of "wrapped" coil curvature is about a central axis 100, which is parallel to the major axis of the coil ellipse. And FIG. 15 schematically depicts a coil-58' relationship wherein the cylindrically arcuate curvature of the coils is parallel to the minor axis of each coil. In both cases, the typical resultant treatment-zone section is suggested by dashed outline in the front view (FIG. 14a and FIG. 15a).

For purposes of deducing central magnetic-field distribution between opposed coils 58, their major-axis regions (designated p-q-p'-q' in FIG. 7) may be deemed to be at maximum separation $S_1$ and their minor-axis regions (designated m-n-m'-n' in FIG. 7) may be deemed to be at minimum separation $S_2$, as viewed in FIG. 14b. This being the case, major-axis-region contributions to the magnetic field may be deemed to apply for the span S (of FIG. 13) equal to $S_1$ (of FIG. 14b) in the context of an effective inside diameter $D_{maj}$ which corresponds to the major axis of the ellipse; by the same token, minor-axis-region contributions to the magnetic field may be deemed to apply for a span $S_2$ (of FIG. 15b) in the context of an effective inside diameter $D_{min}$ which corresponds to the minor axis of the ellipse. For sectional considerations at planes intermediate those of the major axes and of the minor axes, the field will follow distribution considerations intermediate those controlling distribution in planes of the major axes and of the minor axes, respectively.

Reasoning applied above as to magnetic-field distribution for the FIG. 14 configuration can also be applied to that of FIG. 15, except of course that patterns will differ by reason of the cylindrical curvature about an axis parallel to the minor elliptical axis.

Figure 16:
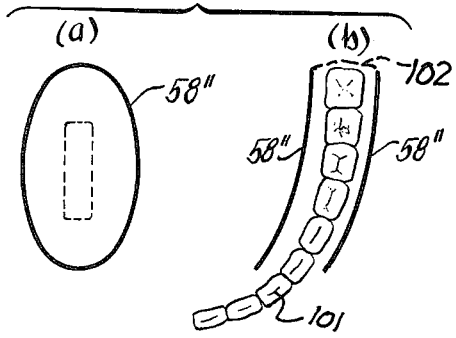

The arrangement of FIG. 16 depicts use of two generally cylindrically arcuate coils 58'' wherein the cylindrical arcs are nested in spaced relation appropriate to the desired application, electrical connection being again understood to be for flux-aiding. The coil arrangement of FIG. 16 will be understood to have application over a generally cylindrically arcuate treatment zone, as in the case of a jaw segment or group of teeth, the latter being suggested schematically at 101 in FIG. 16b. Depending upon the size of coils 58'', it will be understood that they may be retained in fixed spacing, using a suitable bracket (suggested at 102) which bridges only teeth in the case of insertion of both coils in the mouth, and which bridges teeth as well as the adjacent cheek (via the mouth) in the case of one coil inside and the other coil outside the mouth. It will also be understood that for purposes of certain desired flux distribution within the mouth, as for dental and/or jaw osteogenesis, the inner coil 58'' may be of smaller physical size than the outer coil 58''.

It will be understood that the foregoing discussion of general principles is with a view to illustration and not limitation, and that modifications may be made without departing from the scope of the invention. For example, if for certain purposes, it is not possible to construct both coils of a dual-coil embodiment so as to completely match in geometry and electrical properties, as suggested above for a dental or jaw application, there can still be a useful employment of the invention, using magnetic-flux distribution which may not be as uniform as discussed in connection with FIGS. 13 to 16, but which nevertheless derives benefit from the flux-aiding cooperation of two coils in opposite sides of the afflicted region under treatment, such benefit flowing of course from the excitation of such coils by the specially characterized inputs discussed in connection with FIGS. 4 to 6.

FIGS. 17 to 20 are concerned with coil configurations applicable to flux development along and therefore generally parallel to the longitudinal direction of a body member to be treated. In FIG. 17, a single coil of like plural turns 105 is helically developed along the length of a supporting tubular member 106 of suitable plastic or other non-magnetic material. The turns 105 may be on the inner or the outer surface of tube 106, and the axial length of the winding should be such as to overlap both longitudinal ends of the bone fracture or the like to be treated.

In FIG. 18, a single winding is again shown carried by one of the cylindrical surfaces of a tubular member 108, but the latter is locally cut at an opening 109 (as in the manner described at 81 in FIG. 11) to permit insertion of a joint region such as the elbow, with the forearm projecting out one axial end of tubular member 108, and with the upper arm projecting radially outward via opening 109. The single winding is shown as a first plurality 110 of helical turns continuously connected by an axially expanded turn 111 to a second plurality 112 of similar turns, the pluralities 110-112 being positioned on opposite longitudinal sides of the opening 109 and at a spacing which is at least no greater than the effective diameter of the turns 110-112.

The arrangement of FIG. 19 is similar to that of FIG. 18 except that the respective pluralities of turns 110-112 are electrically connected in parallel, in flux-aiding relation. A central access port will be understood to be provided in tubular member 108 at a location opposite the opening 109, to permit excitation wiring connections to be provided external to all turns, i.e., no supply lines passing within any of the turns at 110-112.

In the arrangement of FIG. 20, two coil subassemblies 115-116 are constructed for assembly to the respective ends of a longitudinally split compliant-supporting member 117 of non-magnetic material. The longitudinal split at 118 permits a degree of flexibility in application to a body member, as for example during the course of its assembly past the heel region to a leg part to be treated. Each of the coil subassemblies is shown to be a relatively rigid annular assembly of a winding to a potting of cured hardenable material, and formed with a counterbore 119 at which the coil subassembly is telescopically assembled over the end of the adjacent end of tubular member 117. The inner end of each counterbore defines an inward flange to limit coil assembly, and to determine repeatably accurate spaced retention of the two coil subassemblies. Electrical connections to the coil subassemblies are shown to be parallel, and should be in flux-aiding relation, and a flexible-cable interconnection is suggested at 120.

It will be understood that various simplifying techniques have been adopted to make for more readily understood reference to the drawings. For example, in the rigid-frame coil-supporting embodiments of FIGS. 11, 12, and 17 to 20, it will be understood that in application to the body certain cushioning liner materials such as urethane foam are preferably adhered to the described structure for comfortable engagement with the body at the region of application, but to have shown such liners would only encumber the drawings. Also, in connection with FIG. 9, the showing of the cast 71 is merely illustrative, in that the key device 65 may be otherwise externally mounted, as for example to an external fixation device such as a puttee, or to the body limb itself (i.e., without a cast, as in latter stages of a bone repair), and the cast may be of materials other than plaster, e.g., the material known as orthoplast.

What is claimed is:

1. An electromagnetic body-treatment device for surgically non-invasive modification of the growth, repair and maintenance behavior of living tissues and cells by a specific and selective change in electrical environment, comprising two multi-turn electrical coils and body-adapting retaining means adapted to mount said coils in spaced relation on opposite sides of an afflicted body region to be treated, said coils when thus mounted having turns about a flux-development axis through the afflicted body region and being connected in flux-aiding relation, said turns being radially spaced from said axis to an extent establishing an effective local diameter which substantially equals or exceeds the effective axial spacing between said coils, and means for electrically exciting said coils with a succession of low-voltage unidirectional asymmetrical pulses.

2. The treatment device of claim 1, in which said retaining means comprises strap means adapted for circumferential wrap of the afflicted body region, said coils being mounted to and along said strap means in spaced relation such as to position said coils on opposite sides of the body-treatment region when said strap means is in circumferentially wrapped application to the body.

3. The treatment device of claim 2, in which said strap means is flexible and includes means for selectively adjusting the strap-connected span between said coils.

4. The treatment device of claim 3, in which said strap means is of length extending beyond the adjustably connected span in an amount at least sufficient for full circumferential envelopment of said adjustably connected span, and selectively operable means for securing said strap means in the position of such circumferential envelopment.

5. The treatment device of claim 1, in which at least one of said coils is of generally elliptical configuration.

6. The treatment device of claim 5, in which said elliptical coil is developed in essentially a single surface which is generally cylindrically arcuate.

7. The treatment device of claim 6, in which the arcuate curvature is about an axis generally parallel to the major axis of the ellipse.

8. The treatment device of claim 6, in which the arcuate curvature is about an axis generally parallel to the minor axis of the ellipse.

9. The treatment device of claim 1, in which both of said coils are of generally elliptical configuration, and in which said retaining means positions the major-axis orientation of said coils in generally parallel relation.

10. The treatment device of claim 9, in which each of said coils is developed in essentially a single surface which is cylindrically arcuate, said retaining means being adapted to position the concave sides of the respective coils in face-to-face relation across the afflicted region.

11. The treatment device of claim 9, in which each of said coils is developed in essentially a single surface which is cylindrically arcuate about an axis which is generally parallel to the major axis of its ellipse, said retaining means being adapted to position the major axes in generally parallel relation.

12. The treatment device of claim 9, in which each of said coils is developed in essentially a single surface which is cylindrically arcuate about an axis which is generally parallel to the minor axis of its ellipse, said retaining means being adapted to position the minor axes in generally parallel relation.

13. The treatment device of claim 9, in which each of said coils is developed in essentially a single surface which is cylindrically arcuate, said retaining means being adapted to position the concave sides of the respective coils in nested relation, with the concave side of one coil facing the convex side of the other coil across the afflicted region.

14. The treatment device of claim 1, in which both said coils are of generally helical configuration, the helical advance of both coils being in the same direction.

15. The treatment device of claim 1, in which each of said coils comprises plural generally helically advancing turns in the same direction.

16. The treatment device of claim 1, in which said coils are electrically connected in parallel.

17. The treatment device of claim 1, in which said coils are electrically connected in series.

18. The treatment device of claim 1, in which said retaining means comprises a rigid tubular frame member with said respective coils rigidly mounted to said frame member at opposed locations, the wall of said frame member being locally open within the region of mounting one of said coils, whereby a body member having the afflicted region may be removably entered into said frame member and pass through the frame opening to place the afflicted region in the treatment zone of said coils.

19. The treatment device of claim 1, in which said retaining means comprises a rigid tubular frame member with said respective coils rigidly mounted to said frame member at spaced locations, the wall of said frame member being locally open in a region intermediate the mounting of said coils, whereby a body member having the afflicted region may be removably entered into said frame member and pass through the frame opening to place the afflicted region in the treatment zone of said coils.

20. The treatment device of claim 1, in which said retaining means for at least one of said coils includes a prismatic casing of non-magnetic material, said casing having a front surface adapted for orientation in facing adjacency to one side of the body region to be treated, said one coil being located by and within said casing and in adjacency to said front surface, said surface having a keying recess formed therein, the peripheral edge of said recess extending symmetrically about the central axis of said one coil, and a separate key element conforming to and removably insertable in said recess, said key element having laterally extending adapter means for relatively fixed location of said key element with respect to the body to be treated, whereby once correctly located and fixed with respect to the body, said key element will accurately determine the location of said one coil upon assembly of the surface recess thereto, so that said retaining means can then correctly reference both coils to the body-treatment region, for repeated application and removal of said coils with respect to the body.

21. The treatment device of claim 20, in which said key element includes radiologically opaque frame-marking means at peripheral edges of said key element.

22. The treatment device of claim 21, in which said frame-marking means includes a strip of metal tape removably adhered to the peripheral edge of said key element.

23. The treatment device of claim 1, in which said retaining means for at least one of said coils includes a prismatic casing of non-magnetic material, said casing having a front surface adapted for orientation in facing adjacency to one side of the body region to be treated, said one coil being located by and within said casing and in adjacency to said front surface, said surface having a locating key formation therein in symmetrical placement with respect to the central axis of said one coil, and a removably positionable locating element having a surface formation which conforms to and is interengageable with said key formation, said locating element having laterally extending adapter means for relatively fixed location of said location elements with respect to the body to be treated, whereby once correctly located and fixed with respect to the body, said locating element will accurately determine the location of said one coil upon assembly of said key formation thereto, so that said retaining means can then correctly reference both said coils to the body-treatment region, for repeated application and removal of said coils with respect to the body.

24. The method of applying an electromagnetic body-treatment coil to a body region to be treated, said coil including a prismatic casing of non-magnetic material and having a front surface adapted for orientation in facing relation to one side of the body region to be treated, said surface having a keying recess formed therein, the peripheral edge of said recess extending symmetrically about the central axis of said coil, which method comprises selecting a radiologically transparent key element of size to fit and locate in said keying recess, radiologically observing the body region to be treated along an observation-axis aspect which corresponds generally to the aspect of the central axis of the coil when applied to the body, said observation including adjustably positioning said key element near the body and in the path of observation using radiologically opaque means at edges of the key element to provide an observed frame within which the precise region to be treated may be centrally positioned, securing said key element to the body when the central positioning is observed, and then applying said coil to the body by locating the recess in insertion-receiving registration with said key element.

25. An electromagnetic body-treatment coil assembly, comprising a coil winding having a plurality of turns of large effective radius and short axial extent, and a relatively thin two-part housing for said winding, said housing comprising peripherally flanged front and back panel members assembled in registration with their flanged peripheries in telescoped relation, all turns of said winding being supported and confined at the telescoped peripheral region of and within said housing, said front-panel member being concave and generally cylindrically arucate, and said back-panel member being convex with generally the cylindrically arcuate curvature of said front-panel member, said winding and said peripheries conforming to substantially the same course and said flanges receiving and locating said winding.

26. The coil assembly of claim 25, in which said coil winding is of generally elliptical course, and said panels are arcuate about an axis that is substantially parallel to the major-axis direction of the winding ellipse.

27. The coil assembly of claim 25, in which said front panel has a central inwardly-cupped prismatic recess formation for removable reception of a body-mounted locating key, said recess formation being symmetrically positioned with respect to the central axis of said coil winding.

28. An electromagnetic body-treatment device for surgically non-invasive modification of the growth, repair and maintenance behavior of living tissues and cells by a specific and selective change in electrical environment, comprising magnetic-circuit means including two spaced elements and body-adapting retaining means adapted to mount said elements in spaced relation on opposite sides of an afflicted body region to be treated, said elements being adapted when thus mounted to establish a flux-development axis therebetween and through the afflicted body region, and electric-circuit means for exciting said magnetic-circuit means with a succession of low-voltage unidirectional asymmetrical pulses, the effective sectional area of said elements being such in relation to the spacing of said elements when thus mounted as to enable establishment of a substantially uniform flux distribution throughout a major fraction of the geometrical volume defined by and between said elements.

29. An electromagnetic body-treatment device for surgically non-invasive modification of the growth, repair and maintenance behavior of living tissues and cells by a specific and selective change in electrical environment, comprising a multi-turn electrical coil and body-adapting retaining means adapted to mount said coil in external adjacency to an afflicted body region to be treated, said coil when thus mounted having turns about a flux-development axis to be aligned through the afflicted body region, said retaining means including a prismatic casing of non-magnetic material, said casing having a front surface adapted for orientation in facing adjacency to one side of the body region to be treated, said coil being located by and within said casing and in adjacency to said front surface, said surface having a locating key formation therein in symmetrical placement with respect to the central axis of said coil, and a removably positionable locating element having a surface formation which conforms to and is interengageable with said key formation, said locating element having laterally extending adapter means for relatively fixed location of said locating element with respect to the body to be treated, whereby once correctly located and fixed with respect to the body, said locating element will accurately determine the location of said coil upon assembly of said key formation thereto, so that said retaining means can then correctly reference said coil to the body-treatment region, for repeated application and removal of said coil with respect to the body.

30. The treatment device of claim 29 in which said locating key formation is a keying recess in said front surface, and in which the surface formation of said locating element is a key that is removably enterable in said recess.

31. The method of applying an electromagnetic body-treatment coil to a body region to be treated, said coil including a prismatic casing of non-magnetic material and having a front surface adapted for orientation in facing relation to one side of the body region to be treated, said surface having a locating key formation therein in symmetrical placement with respect to the central axis of said coil, which method comprises selecting a radiologically transparent key element having a surface formation which conforms to and is interengageable with said key formation, said key element having a radiologically opaque marking which is symmetrical about the central axis of the coil when said key element is in locating engagement with said key formation, radiologically observing the body region to be treated along an observation-axis aspect which corresponds generally to the aspect of the central axis of the coil when applied to the body, said observation including adjustably positioning said key element near the body and in the path of observation using said radiologically opaque marking to provide a frame-centering reference with respect to which the precise region to be treated may be correctly positioned, securing said key element to the body when the correct positioning is observed, and then applying said coil to the body by manipulating said key formation into locating engagement with said key element.

* * * * *